(12) United States Patent
Luengo et al.

(10) Patent No.: US 6,630,470 B1
(45) Date of Patent: Oct. 7, 2003

(54) G-CSF MIMETICS

(75) Inventors: Juan I Luengo, Audubon, PA (US); Kevin J Duffy, Norristown, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/700,825

(22) PCT Filed: May 20, 1999

(86) PCT No.: PCT/US99/11143
§ 371 (c)(1),
(2), (4) Date: Nov. 20, 2000

(87) PCT Pub. No.: WO99/61445
PCT Pub. Date: Dec. 2, 1999

Related U.S. Application Data

(60) Provisional application No. 60/086,489, filed on May 22, 1998.

(51) Int. Cl.⁷ .................. C07D 487/22; C07D 498/22; C07D 513/22; A61K 31/415; A61K 31/42

(52) U.S. Cl. ............... 514/246; 544/209; 544/211; 544/212; 544/213; 548/156; 548/222; 548/305.4

(58) Field of Search ................ 544/209, 211, 544/212, 213; 514/246; 548/156, 222, 305.4

(56) References Cited

U.S. PATENT DOCUMENTS 5,981,551 A * 11/1999 Luengo et al. .............. 514/333

FOREIGN PATENT DOCUMENTS

WO        WO 97/44033        * 11/1997

* cited by examiner

*Primary Examiner*—Richard L. Raymond
*Assistant Examiner*—Venkataraman Balasubramanian
(74) *Attorney, Agent, or Firm*—Wayne J. Dustman; Stephen Venetianer; Charles M. Kinzig

(57) ABSTRACT

Invented are G-CSF mimetics. Also invented are selected octacyclic compounds, pharmaceutical compositions containing these compounds, and methods of using these compounds as G-CSF mimetics. Also invented are novel processes used in preparing these compounds.

10 Claims, No Drawings

G-CSF MIMETICS

This is a 371 of International Application PCT/US99/11143, filed May 20, 1999, which claims benefit from the following U.S. Provisional Application: No. 60/086,489, filed May 22, 1998.

BACKGROUND OF THE INVENTION

Granulocyte colony-stimulating factor (G-CSF) is a glycoprotein secreted by macrophages, fibroblasts, and endothelial cells originally identified by its ability to stimulate the survival, proliferation, and differentiation in vitro of predominantly neutrophilic granulocytes from bone marrow progenitors. Nicola, N. A., *Annu. Rev. Biochem.* (1989) 58:45. The capacity of G-CSF to regulate in vivo granulopoiesis is supported by animal and clinical studies, which demonstrated a reversible rise in circulating neutrophil levels in response to administered recombinant G-CSF. Gabrilove, J. L. et al., *N. Engl. J. Med.* (1988) 318:1414. G-CSF has pleiotropic effects on mature neutrophils, enhancing their survival and stimulating functional activation, including induction of neutrophil alkaline phosphatase (Sato. N. et al., *J. Cell. Physiol.* (1988) 37:272) and high affinity IgA $F_c$ receptors (Weisbart, R. H., et al., *Nature* (Lond.) (1988) 332:647), priming for respiratory burst (Nathan, C. F. *Blood* (1989) 73:301) and increased chemotaxis (Wang, J. M., *Blood* (1988) 72:1456). G-CSF effects have also been observed on hematopoietic cells that are not committed to the granulocyte lineage, for example, stimulation of the proliferation on monocytic differentiation in vitro of some myeloid leukemic cells (Geissler, K., *J. Immunol.* (1989) 143:140) and the proliferation in vitro of some multipotential hematopoietic precursors (Ferrero, D., *Blood* (1989) 73:402).

Administration of recombinant G-CSF to patients suffering from neutropenia due to various causes indicated that G-CSF is beneficial as an adjuvant in chemotherapy and in bone marrow transplantation (Morstyn, G., et al., *Trends Pharmacol. Sci.* 10, (1989) 154–159). G-CSF activity is also associated with mobilization of hematopoietic stem cells from the marrow to the peripheral blood. (See review article, Good Review article Haylock et al., *Blood* 89:2233–2258, 1997).

It would be desirable to provide compounds which allow for the treatment of neutropenia to enhance leukocyte production by acting as a G-CSF mimetics.

As disclosed herein it has unexpectedly been discovered that certain octacyclic compounds are effective as G-CSF mimetics.

SUMMARY OF THE INVENTION

This invention relates to compounds of Formula (1):

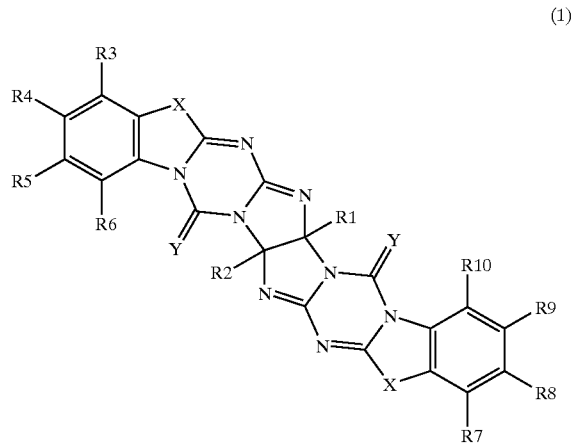

(1)

wherein $R^1$ and $R^2$ are independently aryl, where aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: $C(O)NR^{11}R^{12}$, $NR^{11}R^{12}$, aryloxy, cycloalkyl, substituted cycloalkyl, alkyl, $C_6$–$C_{12}$aryl, alkoxy, acyloxy, substituted $C_6$–$C_{12}$aryl, trifluoromethyl, methoxycarbonyl, amino, N-acylamino, nitro, cyano, halogen, hydroxy, —C(O)OR$^{11}$, —S(O)$_2$NR$^{11}$R$^{12}$, —S(O)$_n$R$^{13}$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^{11}$, —S(O)$_2$NR$^{11}$R$^{13}$, —S(O)$_n$R$^{13}$, aryloxy, nitro, cyano, halogen and protected —OH, where $R^{11}$ and $R^{12}$ are independently hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^{13}$, —S(O)$_n$R$^{13}$, C(O)N(R$^{13}$)$_2$, S(O)$_2$N(R$^{13}$)$_2$, nitro, cyano, cycloalkyl, substituted cycloalkyl, halogen, $C_6$–$C_{12}$aryl. substituted $C_6$–$C_{12}$aryl and protected —OH, n is 0–2, $R^{13}$ is hydrogen, alkyl, cycloalkyl, $C_6$–$C_{12}$aryl, substituted alkyl, substituted cycloalkyl and substituted $C_6$–$C_{12}$aryl;

$R^3$, $R^4$, $R^5$, $R^6$, $R^7$, $R^8$, $R^9$ and $R^{10}$ are independently hydrogen, $C(O)NRC_{11}R^{12}$, $NR^{11}R^{12}$, aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^{11}$, —S(O)$_2$NR$^{11}$R$^{12}$, —S(O)$_n$R$^{13}$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^{11}$, —S(O)$_2$NR$^{11}$R$^{12}$, —S(O)$_n$R$^{13}$, aryloxy, nitro, cyano, halogen and protected —OH, where $R^{11}$, n, $R^{12}$ and $R^{13}$ are as described above;

X is O, S or NR$^{11}$, where R$^{11}$ is as described above; and

Y is O or S; and pharmaceutically acceptable salts, hydrates, solvates and esters thereof.

The present invention also relates to the discovery that the compounds of Formula (I) are active as G-CSF mimetics.

The invention also is a method for treating neutropenia, including chemotherapy-induced neutropenia and bone marrow transplantation and in mobilizing peripheral blood stem cells and other conditions with depressed leukocyte production in mammals, including humans, which comprises administering to a subject in need thereof an effective amount of a presently invented G-CSF mimetics compound.

The invention is also a method for treating bacterial and fungal infections in mammals, including humans, which comprises administering to a subject in need thereof an effective amount of a presently invented G-CSF mimetics compound.

In a further aspect of the invention there is provided novel processes useful in preparing the presently invented G-CSF mimetics compounds.

Included in the present invention are pharmaceutical compositions comprising a pharmaceutical carrier and compounds useful in the methods of the invention.

Also included in the present invention are methods of co-administering the presently invented G-CSF mimetics compounds with further active ingredients.

DETAILED DESCRIPTION OF THE INVENTION

The compounds of this invention that act as G-CSF mimetics have the following Formula (1):

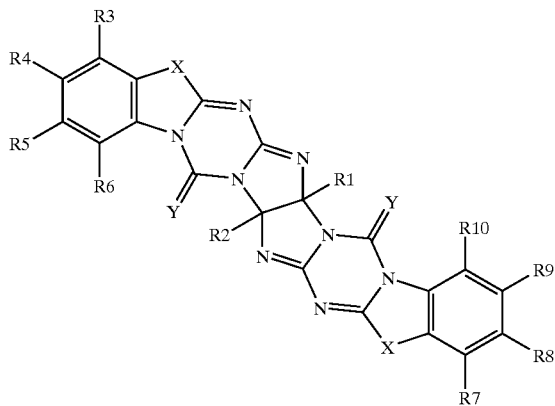

(1)

wherein R$^1$ and R$^2$ are independently aryl, where aryl is cyclic or polycyclic aromatic C$_3$–C$_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: C(O)NR$^{11}$R$^{12}$, NR$^{11}$R$^{12}$, aryloxy, cycloalkyl, substituted cycloalkyl, alkyl, C$_6$–C$_{12}$aryl, alkoxy, acyloxy, substituted C$_6$–C$_{12}$aryl, trifluoromethyl, methoxycarbonyl, amino, N-acylamino, nitro, cyano, halogen, hydroxy, —C(O)OR$^{11}$, —S(O)$_2$NR$^{11}$R$^{12}$, —S(O)$_n$R$^{13}$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^{11}$, —S(O)$_2$NR$^{11}$R$^{12}$, —S(O)$_n$R$^{13}$, aryloxy, nitro, cyano, halogen and protected —OH, where R$^{11}$ and R$^{12}$ are independently hydrogen, cycloalkyl, C$_6$–C$_{12}$aryl, substituted cycloalkyl, substituted C$_6$–C$_{12}$aryl, alkyl or alkyl substituted with one or more substituents selected from the group consisting of: alkoxy, acyloxy, aryloxy, amino, N-acylamino, oxo, hydroxy, —C(O)OR$^{13}$, —S(O)$_n$R$^{13}$, C(O)N(R$^{13}$)$_2$, S(O)$_2$N(R$^{13}$)$_2$, nitro, cyano, cycloalkyl, substituted cycloalkyl, halogen, C$_6$–C$_{12}$aryl, substituted C$_6$–C$_{12}$aryl and protected —OH, n is 0–2, R$^{13}$ is hydrogen, alkyl, cycloalkyl, C$_6$–C$_{12}$aryl, substituted alkyl, substituted cycloalkyl and substituted C$_6$–C$_{12}$aryl;

R$^3$, R$^4$, R$^5$, R$^6$, R$^7$, R$^8$, R$^9$ and R$^{10}$ are independently hydrogen, C(O)NR$^{11}$R$^{12}$, NR$^{11}$R$^{12}$, aryloxy, cycloalkyl, substituted cycloalkyl, alkyl, C$_6$–C$_{12}$aryl, alkoxy, acyloxy, substituted C$_6$–C$_{12}$aryl, amino, N-acylamino, nitro, cyano, halogen, hydroxy, —C(O)OR$^{11}$, —S(O)$_2$NR$^{11}$R$^{12}$, —S(O)$_n$R$^{13}$, protected —OH and alkyl substituted with one or more substituents selected from the group consisting of: alkoxy, acyloxy, C$_6$–C$_{12}$aryl, substituted C$_6$–C$_{12}$aryl, amino, N-acylamino, oxo, hydroxy, cycloalkyl, substituted cycloalkyl, —C(O)OR$^{11}$, —S(O)$_2$NR$^{11}$R$^{12}$, —S(O)$_n$R$^{13}$, aryloxy, nitro, cyano, halogen and protected —OH, where R$^{11}$, n, R$^{12}$ and R$^{13}$ are as described above;

X is O, S or NR$^{11}$, where R$^{11}$ is as described above; and

Y is O or S; and pharmaceutically acceptable salts, hydrates, solvates and esters thereof.

Preferred among the presently invented Formula I compounds are those in which aryl is: C$_5$–C$_{12}$aryl, optionally containing one or two heteroatoms and optionally substituted with one or more substituents selected from the group consisting of: —OC$_6$–C$_{12}$aryl, —(C$_2$)$_m$OH, C$_6$–C$_{12}$aryl, C$_1$–C$_4$alkyl, —OC$_1$–C$_4$alkyl, amino, nitro, cyano, methoxycarbonyl, N-acylamino, trifluoromethyl, C$_{3-7}$cycloalkyl, halogen, —(CH$_2$)$_p$COOH, —S(O)$_n$R$^{13}$ and protected —OH, where m is 0–4, p is 0–3, n is 0–2 and R$^{13}$ is hydrogen or C$_{1-4}$alkyl; and pharmaceutically acceptable salts, hydrates, solvates and esters thereof.

Particularly preferred among the presently invented compounds are those in which R$^1$ and R$^2$ are independently phenyl, naphthyl, furyl, thienyl, pyridyl, indolyl or quinolyl all of which are unsubstituted or substituted with a substituent selected from the group consisting of: halogen, C$_{1-5}$alkyl, trifluoromethyl, —COOH, methoxycarbonyl, C$_{3-7}$cycloalkyl and —O—C$_{1-4}$alkyl;

R$^3$, R$^4$, R$^5$, R$^6$, R$^7$, R$^8$, R$^9$ and R$^{10}$ are independently hydrogen, —OC$_6$–C$_{12}$aryl, C$_6$–C$_{12}$aryl, C$_1$–C$_4$alkyl, —OC$_1$–C$_4$alkyl, amino, nitro, cyano, N-acylamino. C$_{3-7}$cycloalkyl, halogen, —S(O)$_n$R$^{13}$ or protected —OH, where m is 0–4, p is 0–3, n is 0–2 and R$^{13}$ is hydrogen or C$_{1-4}$alkyl; and pharmaceutically acceptable salts, hydrates, solvates and esters thereof.

Particularly preferred among the presently invented compounds are those in which R$^1$ and R$^2$ are independently phenyl, furyl, thienyl or pyridyl all of which are unsubstituted or substituted with a substituent selected from the group consisting of: halogen, $C_{1-5}$alkyl, trifluoromethyl, —COOH, methoxycarbonyl, $C_{3-6}$cycloalkyl and —O—$C_{1-3}$alkyl;

$R^3$, $R^4$, $R^5$, $R^6$, $R^7$, $R^8$, $R^9$ and $R^{10}$ are independently hydrogen, halogen, $C_{1-5}$alkyl, $C_{3-7}$cycloalkyl or —O—$C_{1-4}$alkyl; and pharmaceutically acceptable salts, hydrates, solvates and esters thereof.

The most preferred compounds of the present invention are those in which $R^1$ and $R^2$ are independently phenyl, furyl or pyridyl all of which are unsubstituted or substituted with a substituent selected from the group consisting of: halogen, $C_{1-5}$alkyl, trifluoromethyl, —COOH, methoxycarbonyl and —O—$C_{1-3}$alkyl; and $R^3$, $R^4$, $R^5$, $R^6$, $R^7$, $R^8$, $R^9$ and $R^{10}$ are independently hydrogen, trifluoromethyl, methoxycarbonyl, halogen or $C_{1-3}$alkyl; and pharmaceutically acceptable salts, hydrates, solvates and esters thereof.

Preferred among the presently invented compounds are:

Compound A: 7a,17a-bis(2-pyridyl)-6,16-dioxo-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazol;

Compound B: 6,16-dioxo-7a,17a-diphenyl-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazole;

Compound E: 7a,17a-bis(4-fluorophenyl)-6,16-dioxo-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazole;

Compound G: 7a,17a-bis(4-bromophenyl)-6,16-dioxo-6,7a,10,16,17a,20-hexahydro-benezimidazo[2',1':4,5][1,3,5]triazino[1,2-a]benzimidazo[2",1":4',5'][1,3,5]triazino[2'1':2,3]imidazo[4,5-d]imidazole;

Compound H: 7a,7a-bis(2-pyridyl)-6,16-dithiono-6,7a,10,16,17a,20-hexahydro-benzimidazo[2",1':4,5][1,3,5]triazino[1,2-a]benzimidazo[2",1":4',5'][1,3,5]triazino[2',1':2,3]imidazo[4,5-d]imidazole and pharmaceutically acceptable salts, hydrates, solvates and esters thereof.

By the term "protected hydroxy" or "protected —OH" as used herein, is meant the alcoholic or carboxylic-OH groups which can be protected by conventional blocking groups in the art as described in "Protective Groups In Organic Synthesis" by Theodora W. Greene, Wiley-Interscience, 1981, New York.

By the term "$C_5$–$C_{12}$ aryl" as used herein, unless otherwise defined, is meant a cyclic or polycyclic aromatic $C_5$–$C_{12}$ optionally containing one or two heteroatoms.

By the term "$C_6$–$C_{12}$ aryl" as used herein, unless otherwise defined, is meant phenyl, naphthyl, 3,4-methylenedioxyphenyl, pyridyl, or biphenyl.

By the term "substituted" as used herein, unless otherwise defined, is meant that the subject chemical moiety has one or more substituents selected from the group consisting of: hydroxyalkyl, alkoxy, acyloxy, alkyl, amino, N-acylamino, hydroxy, —$(CH_2)_gC(O)OR^{11}$, —$S(O)_2NR^{11}R^{12}$, —$S(O)_nR^{12}$, nitro, cyano, halogen, trifluoromethyl and protected —OH, where g is 0–6, $R^{11}$ is hydrogen or alkyl, n is 0–2, and $R^{12}$ is hydrogen or alkyl.

By the term "alkoxy" as used herein is meant -Oalkyl where alkyl is as described herein including —$OCH_3$ and —$OC(CH_3)_2CH_3$.

The term "cycloalkyl" as used herein unless otherwise defined, is meant a nonaromatic, unsaturated or saturated, cyclic or polycyclic $C_3$–$C_{12}$.

Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —N(H)C(O)alkyl, where alkyl is as described herein. Examples of N-acylamino substituents as used herein include: —$N(H)C(O)CH_3$, —$N(H)C(O)CH(CH_3)_2$ and —$N(H)C(O)(CH_2)_3CH_3$.

By the term "aryloxy" as used herein is meant —$OC_6$—$C_{12}$aryl where $C_6$–$C_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —$(CH_2)_gC(O)OR^{11}$, —$S(O)_nR^{12}$, nitro, cyano, halogen and protected —OH, where g is 0–6, $R^{11}$ is hydrogen or alkyl, n is 0–2 and $R^{12}$ is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain having $C_1$–$C_{12}$ carbon atoms. Examples of alkyl substituents as used herein include: —$CH_3$, —$CH_2$—$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$ and —$CH(CH_3)$—$CH_2$—$CH_3$, —$CH=CH_2$.

By the term "treating" and derivatives thereof as used herein, is meant prophylatic or therapeutic therapy.

By the phrase "mobilizing peripheral blood stem cells" as used herein is meant the mobilization of hematopoietic stem cells from the marrow to the peripheral blood.

All publications, including but not limited to patents and patent applications, cited in this specificaiton are herein incorporated by reference as if each individual publicaiton were specifically and individually indicated to be incorporated by reference herein as though fully set forth.

Compounds of Formula (1) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

By the term "co-administering" and derivatives thereof as used herein is meant either simultaneous administration or any manner of separate sequential administration of a G-CSF mimetic compound, as described herein, and a further active ingredient or ingredients, such as antibacterial agents, antifungal agents as well as agents known to treat neutropenia, including chemotherapy-induced neutropenia and bone marrow transplantation and in mobilizing peripheral blood stem cells and other conditions with depressed leukocyte production. Preferably, if the administration is not simultaneous, the compounds are administered in a close time proximity to each other. Furthermore, it does not matter if the compounds are administered in the same dosage form, e.g. one compound may be administered topically and another compounds may be administered orally.

The novel compounds of Formula (I) are prepared as shown in Scheme I below provided that the 'R'. X and Y substituents do not include any such substituents that render inoperative the Scheme I process. The compounds of Formula (2) are prepared by methods analogous to the Schemes and Examples used to prepare the Formula (I) compounds in International Application PCT/US97/08864. Published on Nov. 27, 1997 as WO 97/44033. The reagents used herein are commercially available or are readily made by those skilled in the art from commercially available materials.

Scheme (I)

Preparation of Compounds of Formula (1)

Compounds of Formula (2)

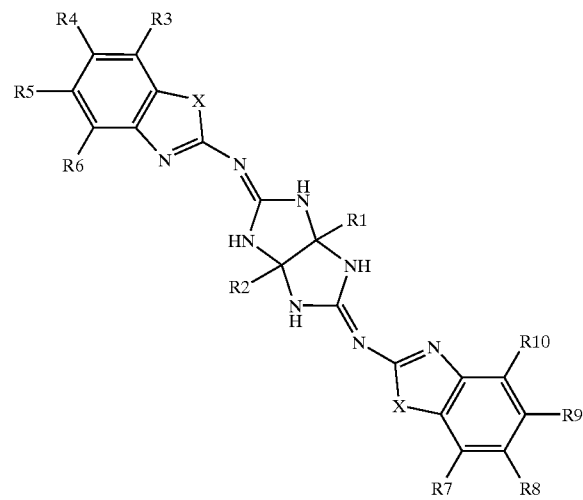

wherein $R^1$, $R^2$, $R^3$, $R^4$, $R^5$, $R^6$, $R^7$, $R^8$, $R^9$, $R^{10}$ and X are as described in Formula (I) above, are reacted with phosgene or thiophosgene or an appropriate phosgene or thiophosgene equivalent such as bistrichloromethyl carbonate, disuccinidimoyl carbonate, carbonyl diimidazole or thiocarbonyl dimidazole in an appropriate solvent, preferably pyridine or 1,2-dichloroethane, to afford octacyclic compounds of Formula (1),

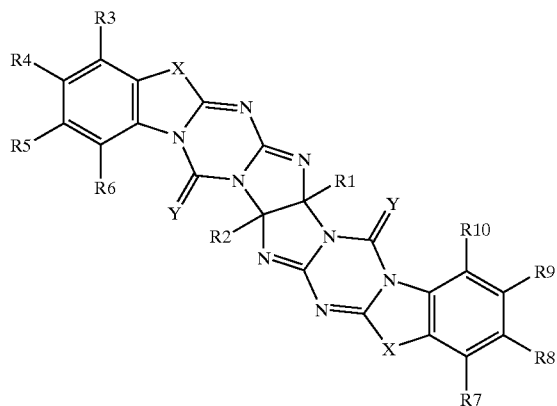

wherein $R^1$, $R^2$, $R^3$, $R^4$, $R^5$, $R^6$, $R^7$, $R^8$, $R^9$, $R^{10}$, Y and X are as described in Formula (1) above; or a mixture comprising a compound of Formula (1) and a compound of Formula (3)

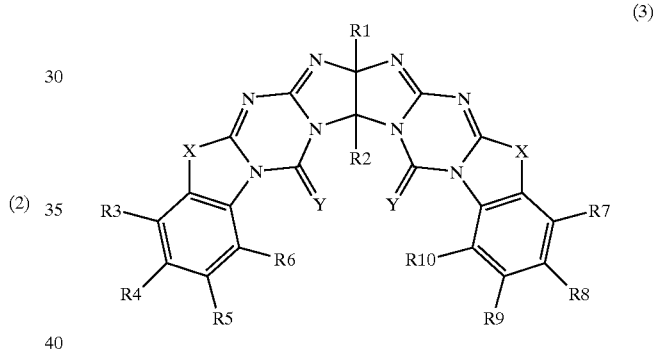

wherein $R^1$, $R^2$, $R^3$, $R^4$, $R^5$, $R^6$, $R^7$, $R^8$, $R^9$, $R^{10}$, Y and X are as described in Formula (1) above. The mixtures of compounds of Formulas (1) and (3) are readily separated by chromatography.

Pharmaceutically acceptable salts, hydrates and solvates are formed when appropriate by methods well known to those of skill in the art.

Because the pharmaceutically active compounds of the present invention are active as G-CSF mimetics they exhibit therapeutic utility in treating bacterial infections, fungal infections, neutropenia, including chemotherapy-induced neutropenia and bone marrow transplantation and in mobilizing peripheral blood stem cells and other conditions with depressed leukocyte production.

In determining potency as G-CSF mimetics, the following assay is employed:

CFU-g Assay

The compounds of present invention are tested for potency as G-CSF mimetics in a CFU-g assay, an example of which is described in King A G, Talmadge J., Badger A M, Pelus L M. Regulation of colony stimulating activity production from bone marrow stromal cells by the hematoregulatory peptide, HP-5. *Exp. Hematol.* 20:223–228, 1992.

The pharmaceutically active compounds within the scope of this invention are useful as G-CSF mimetics in mammals, including humans, in need thereof.

The present invention therefore provides a method of treating bacterial infections, fungal infections, neutropenia, including chemotherapy-induced neutropenia and bone marrow transplantation and in mobilizing peripheral blood stem cells and other conditions with depressed leukocyte production, which comprises administering a compound of Formula (1):

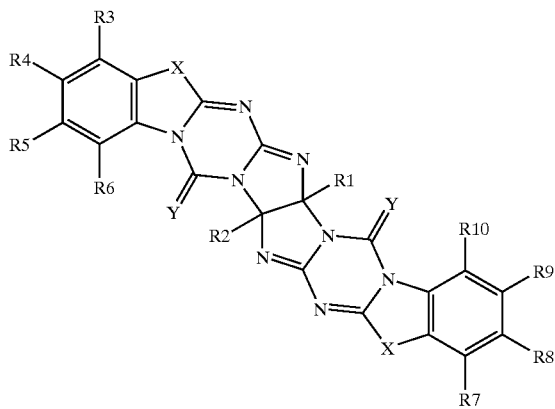

(1)

wherein $R^1$ and $R^2$ are independently aryl, where aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: $C(O)NR^{11}R^{12}$, $NR^{11}R^{12}$, aryloxy, cycloalkyl, substituted cycloalkyl, alkyl, $C_6$–$C_{12}$aryl, alkoxy, acyloxy, substituted $C_6$–$C_{12}$aryl, trifluoromethyl, methoxycarbonyl, amino, N-acylamino, nitro, cyano, halogen, hydroxy, —C(O)OR$^{11}$, —S(O)$_2$NR$^{11}$R$^{12}$, —S(O)$_n$R$^{13}$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^{11}$, —S(O)$_2$NR$^{11}$R$^{12}$, —S(O)$_n$R$^{13}$, aryloxy, nitro, cyano, halogen and protected —OH, where $R^{11}$ and $R^{12}$ are independently hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^{13}$, —S(O)$_n$R$^{13}$, C(O)N(R$^{13}$)$_2$, S(O)$_2$N(R$^{13}$)$_2$, nitro, cyano, cycloalkyl, substituted cycloalkyl, halogen, $C_6$–$C_{12}$aryl, substituted $C_6$–$C_{12}$aryl and protected —OH, n is 0–2, $R^{13}$ is hydrogen, alkyl, cycloalkyl, $C_6$–$C_{12}$aryl, substituted alkyl, substituted cycloalkyl and substituted $C_6$–$C_{12}$aryl;

$R^3$, $R^4$, $R^5$, $R^6$, $R^7$, $R^8$, $R^9$ and $R^{10}$ are independently hydrogen, C(O)NR$^{11}$R$^{12}$, NR$^{11}$R$^{12}$, aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^{11}$, —S(O)$_2$NR$^{11}$R$^{12}$, —S(O)$_n$R$^{13}$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$_{11}$, —S(O)$_2$NR$^{11}$R$^{12}$, —S(O)$_n$R$^{13}$, aryloxy, nitro, cyano, halogen and protected —OH, where R$_{11}$, n, R$^{12}$ and R$^{13}$ are as described above;

X is O, S or NR$^{11}$, where R$^{11}$ is as described above; and

Y is O or S; and pharmaceutically acceptable salts, hydrates, solvates and esters thereof in a quantity effective to enhance leukocyte production. The compounds of Formula (I) also provide for a method of treating the above indicated disease states because of their demonstrated ability to act as G-CSF mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a G-CSF mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg, preferably 0.1 to 350 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular G-CSF mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing G-CSF mimetic activity in mammals, including humans, comprises administering to a subject in need of such activity an effective amount of of a presently invented G-CSF mimetic compound.

The invention also provides for the use of a compound of Formula (I) in the manufacture of a medicament for use as a G-CSF mimetic.

The invention also provides for the use of a compound of Formula (1) in the manufacture of a medicament for use in therapy.

The invention also provides for the use of a compound of Formula (1) in the manufacture of a medicament for use in enhancing leukocyte production.

The invention also provides for the use of a compound of Formula (1) in the manufacture of a medicament for use in treating bacterial and fungal infections.

The invention also provides for a pharmaceutical composition for use as a G-CSF mimetic which comprises a compound of Formula (1) and a pharmaceutically acceptable carrier.

The invention also provides for a pharmaceutical composition for use in the treatment of neutropenia which comprises a compound of Formula (1) and a pharmaceutically acceptable carrier.

The invention also provides for a pharmaceutical composition for use in enhancing leukocyte production which comprises a compound of Formula (1)I and a pharmaceutically acceptable carrier.

The invention also provides for a pharmaceutical composition for use in treating bacterial infections which comprises a compound of Formula (1) and a pharmaceutically acceptable carrier.

The invention also provides for a pharmaceutical composition for use in treating fungal infections which comprises a compound of Formula (1) and a pharmaceutically acceptable carrier.

The invention also provides for a process for preparing a pharmaceutical composition containing a pharmaceutically acceptable carrier or diluent and a compound of Formula (1) which comprises bringing the compound of Formula (1) into association with the pharmaceutically acceptable carrier or diluent.

No unacceptable toxicological effects are expected when compounds of the invention are administered in accordance with the present invention.

In addition, the pharmaceutically active compounds of the present invention can be co-administered with further active ingredients, such as other compounds known to treat bacterial infections, fungal infections, neutropenia, including chemotherapy-induced neutropenia and bone marrow transplantation and in mobilizing peripheral blood stem cells and other conditions with depressed leukocyte production, or compounds known to have utility when used in combination with a G-CSF mimetic or agents known to have utility when used in combination with such G-CSF mimetics.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Example 1

Preparation 7a,17a-bis(2-pyridyl)-6,16-dioxo-6,7a, 10,16,17a,20-hexahydro-benzimidazo[2',1':4,5][1,3, 5]triazino[1,2-a]benzimidazo[2",1":4',5'][1,3,5] triazino[2',1':2,3]imidazo[4,5-d]imidazole

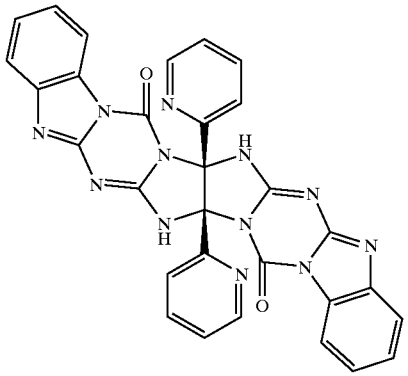

Compound A

A solution of 2,5-bis(2-benzimidazolylimino)-3a,6a-bis (2-pyridyl)-1,2,3,3a,4,5,6,6a-octahydroimidazo[4,5-d] imidazole (2.10 g; 4.0 mmol), prepared as described in Example 1 of International Application PCT/US97/08864, Published on Nov. 27, 1997 as WO 97/44033, and bistrichloromethyl carbonate (4.65 g; 16.0 mmole) in anhydrous 1,2-dichloroethane (25.0 mL) was stirred and heated under reflux for 24 h. The mixture was cooled and filtered and the resulting solid (2.83 g) washed with dichloromethane (100 mL) and dried under vacuum. This solid was dissolved in 6M HCl (50 mL) then 10% aqueous NaOH solution was added (50.0 mL). Filtration afforded the title compound A (0.85 g; 37%) as a yellow solid. $^1$H NMR (300 MHz, $d_6$-DMSO) δ11.8 (s, 2H), 8.39 (d, J=3.8 Hz, 2H), 7.91 (d, J=8.1 Hz, 2H), 7.70–7–60 (m, 4H) and 7.44–7.19 (m, 10H); MS (ESI): 579 [M+H]$^+$; HPLC $t_R$ 6.05 min (ODS-silica, 4.6×250 mm, 2 mL/min, gradient, A: acetonitrile B: water-0.1% trifluoroacetic acid, 20–60% A during 20 min, UV detection at 254 nM).

Further addition of 10% aqueous NaOH solution until pH=14 gave a second precipitate (1.23 g) which was purified by chromatography [ODS-silica, step gradient, 20–40% acetonitrile/water (0.1% TFA)] to afford the triazino[1',2':1, 2]imidazo[4,5-d]imidazole regioisomer, compound C (290 mg; 12%) as a colorless powder. $^1$H NMR (300 MHz, $d_6$-DMSO) δ12.0–10.0 (brs, 2H), 8.44 (d, J=4.1 Hz, 1H), 8.33 (d, J=4.7 Hz, 1H), 7.96 (d, J=7.9 Hz, 2H), 7.67 (td, J=7.9 and 1.4 Hz, 1H), 7.60 (d, J=7.9 Hz, 2H), 7.50–7.27 (m, 8H) and 7.21 (m, 1H); MS (ESI): 579 [M+H]$^+$; HPLC $t_R$ 8.20 min (ODS-silica, 4.6×250 mm, 2 mL/min, gradient, A: acetonitrile B: water-0.1% trifluoroacetic acid, 20–60% A during 20 min, UV detection at 254 nM); Anal. ($C_{30}H_{18}N_{12}$.2$CF_3CO_2H$) calcd: C, 50.6; H, 2.5; N, 20.8. found: C, 50.4; H, 2.6; N, 20.8.

Compound C

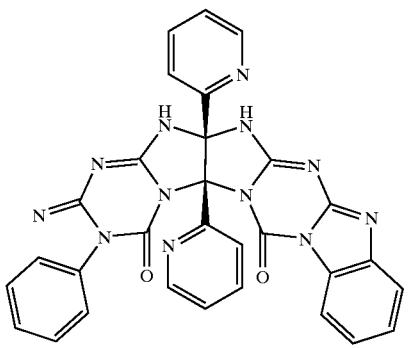

Compound D

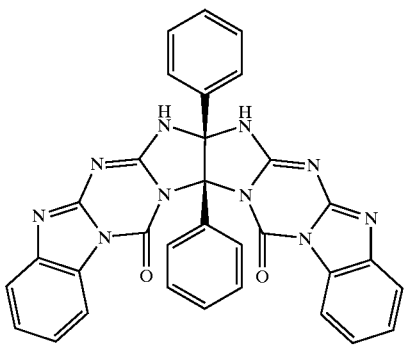

Example 2

Preparation of 6,16-dioxo-7a,17a-diphenyl-6,7a,10,16,17a,20-hexahydro-benzimidazo[2',1':4,5][1,3,5]triazino[1,2-a]benzimidazo[2'',1'':4',5'][1,3,5]triazino[2',1':2,3]imidazo[4,5-d]imidazole Compound B

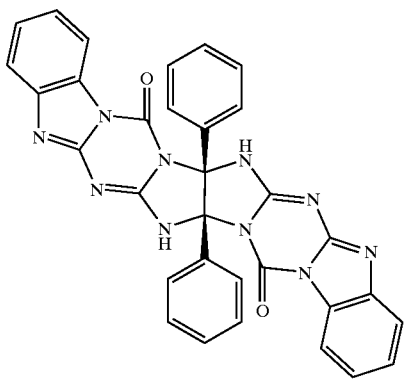

A solution 2,5-bis(2-benzimidazolylimino)-3a,6a-diphenyl-1,2,3,3a,4,5,6,6a-octahydroimidazo[4,5-d]imidazole (262 mg; 0.5 mmol), prepared as described in Example 2 of International Application PCT/US97/08864, Published on Nov. 27, 1997 as WO 97/44033, in anhydrous pyridine (10.0 mL) was treated with phosgene (20% solution in toluene) (2.0 mL; 2.0 mmol) and the mixture stirred at room temperature for 2 days. The mixture was treated with water (5.0 mL) and evaporated to give title compound B and the triazino[1',2':1,2]imidazo[4,5-d]imidazole regioisomer, compound D as a mixture. Compound B (76.5 mg; 27%) MS (ESI): 577 [M+H]$^+$; HPLC $t_R$ 11.95 min (ODS-silica, 4.6× 250 mm, 2 mL/min, gradient, A: acetonitrile B: water-0.1% trifluoroacetic acid, 20–60% A during 20 min, UV detection at 254 nM); Compound D (84.4 mg; 29%) MS (ESI): 577 [M+H]$^+$; HPLC $t_R$ 10.48 min (ODS-silica, 4.6×250 mm, 2 mL/min, gradient. A: acetonitrile B: water-0.1% trifluoroacetic acid, 20–60% A during 20 min, UV detection at 254 nM).

Example 3

Preparation of 7a,17a-bis(4-fluorophenyl)-6,16-dioxo-6,7a,10,16,17a,20-hexahydro-benzimidazo[2',1':4,5][1,3,5]triazino[1,2-a]benzimidazo[2'',1'':4',5'][1,3,5]triazino[2',1':2,3]imidazo[4,5-d]imidazole Compound E

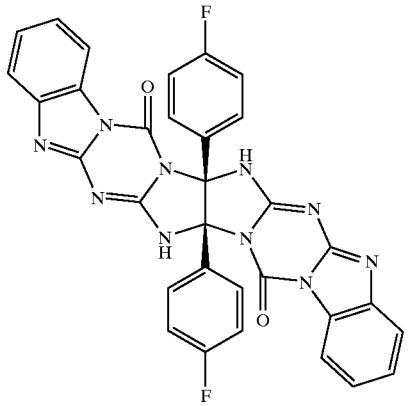

Following the procedure of Example 2 except substituting 2,5-bis(2-benzimidazolylimino)-3a,6a-bis(4-fluorophenyl)-1,2,3,3a,4,5,6,6a-octahydroimidazo[4,5-d]imidazole, prepared as described in Example 6 of International Application PCT/US97/08864, Published on Nov. 27, 1997 as WO 97/44033, for 2,5-bis(2-benzimidazolylimino)-3a,6a-diphenyl-1,2,3,3a,4,5,6,6a-octahydroimidazo[4,5-d]imidazole the title compound E was prepared (30%) along with the triazino[1',2':1,2]imidazo[4,5-d]imidazole regioisomer, compound F (10%) which were separated by chromatography (silica gel, step gradient, 2–7.5% methanol/dichloromethane). Title compound E: MS (ESI): 613 [M+H]$^+$; TLC Rf=0.51 (silica gel, 10% methanol/dichloromethane); Compound F: MS (ESI): 613 [M+H]$^+$; TLC Rf=0.35 (silica gel, 10% methanol/dichloromethane).

Compound F

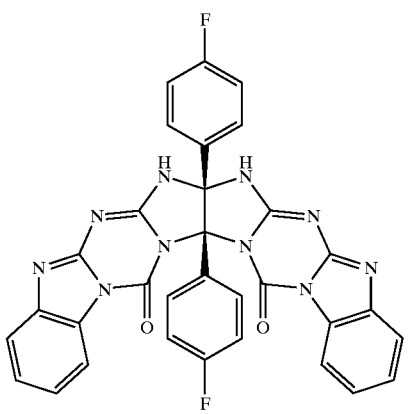

Example 4

Preparation of 7a,17a-bis(4-bromophenyl)-6,16-dioxo-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazole Compound G

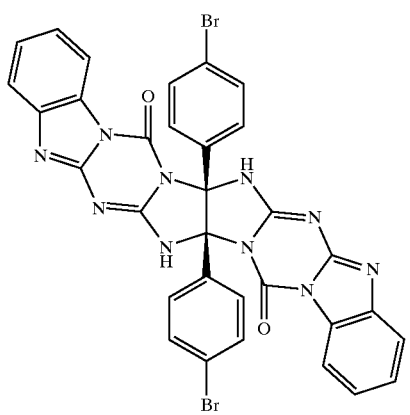

Following the procedure of Example 2 except substituting 2,5-bis(2-benzimidazolylimino)-3a,6a-bis(4-bromophenyl)-1,2,3,3a,4,5,6,6a-octahydroimidazo[4,5-d]imidazole, prepared as described in Example 33 of International Application PCT/US97/08864, Published on Nov. 27, 1997 as WO 97/44033, for 2,5-bis(2-benzimidazolylimino)-3a,6a-diphenyl-1,2,3,3a,4,5,6,6a-octahydroimidazo[4,5-d]imidazole the title compound G was prepared (30%). MS (ESI): 763 [M+H]$^+$.

Example 5

Preparation 7a,17a-bis(2-pyridyl)-6,16-dithiono-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazole Compound H

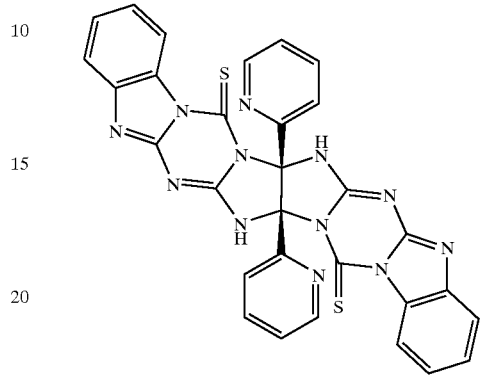

A solution of 2,5-bis(2-benzimidazolylimino)-3a,6a-bis(2-pyridyl)-1,2,3,3a,4,5,6,6a-octahydroimidazo[4,5-d]imidazole (0.12 g; 0.23 mmol), prepared as described in Example 1 of International Application PCT/US97/08864, Published on Nov. 27, 1997 as WO 97/44033, and thiocarbonyl diimidazole (0.18 g; 1.0 mmole) in anhydrous dimethylformamide (5.0 mL) was stirred at room temperature for 24 h. The mixture was treated with water (10 mL) and filtered and the resulting solid dried under vacuum to afford the title compound H (0.089 g; 64%) as a yellow solid. MS (ESI): 641 [M+H]$^+$.

Example 6

Capsule Composition

An oral dosage form for administering a presently invented agonist of the G-CSF receptor is produced by filing a standard two piece hard gelatin capsule with the ingredients in the proportions shown in Table I, below.

TABLE I

| INGREDIENTS | AMOUNTS |
| --- | --- |
| Compound A | 25 mg |
| Lactose | 55 mg |
| Talc | 16 mg |
| Magnesium Stearate | 4 mg |

Example 7

Injectable Parenteral Composition

An injectable form for administering a presently invented agonist of the G-CSF receptor is produced by stirring 1.5% by weight of Compound B in 10% by volume propylene glycol in water.

Example 8

Tablet Composition

The sucrose, calcium sulfate dihydrate and a presently invented agonist of the G-CSF receptor, as shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
| --- | --- |
| Compound A | 20 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of the Formula (1):

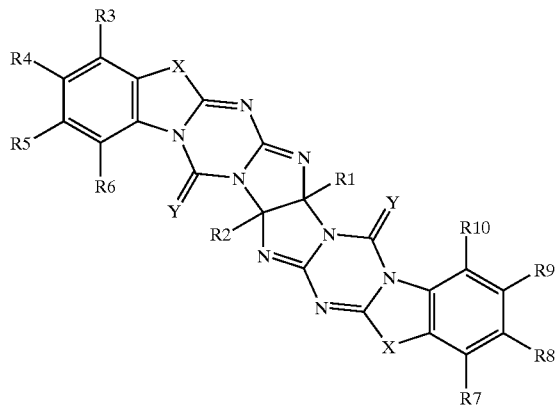

(1)

wherein $R^1$ and $R^2$ are independently aryl,
where aryl is cyclic or polycyclic aromatic $C_3$–$C_{12}$, optionally containing one or more heteroatoms, provided that when C is 3 the aromatic ring contains at least two heteroatoms, and when C is 4 the aromatic ring contains at least one heteroatom, and optionally substituted with one or more substituents selected from the group consisting of: $C(O)NR^{11}R^{12}$, $NR^{11}R^{12}$, aryloxy, cycloalkyl, substituted cycloalkyl, alkyl, $C_6$–$C_{12}$aryl, alkoxy, acyloxy, substituted $C_6$–$C_{12}$aryl, trifluoromethyl, methoxycarbonyl, amino, N-acylamino, nitro, cyano, halogen, hydroxy, —C(O)OR$^{11}$, —S(O)$_2$NR$^{11}$R$^{12}$, —S(O)$_n$R$^{13}$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^{11}$, —S(O)$_2$NR$^{11}$R$^{12}$, —S(O)$_n$R$^{13}$, aryloxy, nitro, cyano, halogen and protected —OH, where
$R^{11}$ and $R^{12}$ are independently hydrogen, cycloalkyl, $C_6$–$C_{12}$aryl, substituted cycloalkyl, substituted $C_6$–$C_{12}$aryl, alkyl or alkyl substituted with one or more substituents selected from the group consisting of: alkoxy, acyloxy, aryloxy, amino, N-acylamino, oxo, hydroxy, —C(O)OR$^{13}$, —S(O)$_n$R$^{13}$, C(O)N(R$^{13}$)$_2$, S(O)$_2$N(R$^{13}$)$_2$, nitro, cyano, cycloalkyl, substituted cycloalkyl, halogen, $C_6$–$C_{12}$aryl, substituted $C_6$–$C_{12}$aryl and protected —OH, n is 0–2,
$R^{13}$ is hydrogen, alkyl, cycloalkyl, $C_6$–$C_{12}$aryl, substituted alkyl, substituted cycloalkyl and substituted $C_6$–$C_{12}$aryl;
$R^3$, $R^4$, $R^5$, $R^6$, $R^7$, $R^8$, $R^9$ and $R^{10}$ are independently hydrogen, C(O)NR$^{11}$R$^{12}$, NR$^{11}$R$^{12}$, aryloxy, cycloalkyl, substituted cycloalkyl, alkyl, $C_6$–$C_{12}$aryl, alkoxy, acyloxy, substituted $C_6$–$C_{12}$aryl, amino, N-acylamino, nitro, cyano, halogen, hydroxy, —C(O)OR$^{11}$, —S(O)$_2$NR$^{11}$R$^{12}$, —S(O)$_n$R$^{13}$, protected —OH and alkyl substituted with one or more substituents selected from the group consisting of: alkoxy, acyloxy, $C_6$–$C_{12}$aryl, substituted $C_6$–$C_{12}$aryl, amino, N-acylamino, oxo, hydroxy, cycloalkyl, substituted cycloalkyl, —C(O)OR$^{11}$, —S(O)$_2$NR$^{11}$R$^{12}$, —S(O)$_n$R$^{13}$, aryloxy, nitro, cyano, halogen and protected —OH, where $R^{11}$, n, $R^{12}$ and $R^{13}$ are as described above;
X is O, S or NR$^{11}$,
where $R^{11}$ is as described above; and
Y is O or S; or
pharmaceutically acceptable salt, hydrate, or solvate thereof.

2. A compound of claim 1 in which aryl is: $C_5$–$C_{12}$aryl, optionally containing one or two heteroatoms and optionally substituted with one or more substituents selected from the group consisting of: —OC$_6$—$C_{12}$aryl, —(CH$_2$)$_m$OH, $C_6$–$C_{12}$aryl, $C_1$–$C_4$alkyl, —OC$_1$–$C_4$alkyl, amino, nitro, cyano, methoxycarbonyl, N-acylamino, trifluoromethyl, $C_{3-7}$cycloalkyl, halogen, —(CH$_2$)$_p$COOH, —S(O)$_n$R$^{12}$ and protected —OH, where m is 0–4, p is 0–3, n is 0–2 and $R^{12}$ is hydrogen or $C_{1-4}$alkyl; or
pharmaceutically acceptable salt, hydrate or solvate thereof.

3. A compound of claim 1 selected from: Compound A; 7a,17a-bis(2-pyridyl)-6,16-dioxo-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazole;

Compound B; 6,16-dioxo-7a,17a-diphenyl-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazole;

Compound E; 7a,17a-bis(4-fluorophenyl)-6,16-dioxo-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazole;

Compound G; 7a,17a-bis(4-bromophenyl)-6,16-dioxo-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazole;

Compound H; 7a,17a-bis(2-pyridyl)-6,16-dithiono-6,7a,10,16,17a,20-hexahydro-benzimidazo[2',1':4,5][1,3,5]triazino[1,2-a]benzimidazo[2",1":4',5'][1,3,5]triazino[2',1':2,3]imidazo[4,5-d]imidazole or pharmaceutically acceptable salt, hydrate, or solvate thereof.

4. A pharmaceutical composition comprising a pharmaceutically acceptable carrier and a compound of claim 1.

5. A method of enhancing leukocyte production in a subject which comprises administering to the subject a therapeutically effective amount of a compound of claim 1.

6. A method of treating neutropenia in a subject which comprises administering to the subject a therapeutically effective amount of a compound of claim 1.

7. A process for the preparation of a compound of Formula (1) as described in claim 1, which comprises reacting a compound of Formula 2

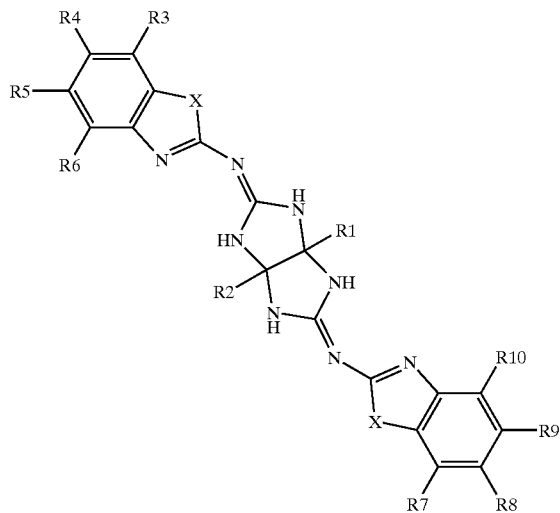

(2)

wherein $R^1$, $R^2$, $R^3$, $R^4$, $R^5$, $R^6$, $R^7$, $R^8$, $R^9$, $R^{10}$ and X are as described in claim 1, with phosgene or thiophosgene or an appropriate phosgene or thiophosgene equivalent in the presence of a solvent, followed by isolation; and thereafter optionally forming a pharmaceutically acceptable salt, hydrate or solvate thereof.

8. A process for preparing a pharmaceutical composition containing a pharmaceutically acceptable carrier or diluent and an effective amount of a compound of the Formula (1) as described in claim 1 and pharmaceutically acceptable salts, hydrates, solvates and esters thereof which process comprises bringing the compound of the Formula (1) into association with the pharmaceutically acceptable carrier or diluent.

9. A method of treating bacterial infections in a subject which comprises administering to the subject a therapeutically effective amount of a compound of claim 1.

10. A method of treating fungal infections in a subject which comprises administering to the subject a therapeutically effective amount of a compound of claim 1.

* * * * *